US006964639B2

(12) United States Patent
Sela et al.

(10) Patent No.: US 6,964,639 B2
(45) Date of Patent: Nov. 15, 2005

(54) SYSTEM AND METHOD OF MAPPING IRREGULARITIES OF HARD TISSUE

(75) Inventors: Natan Sela, Rehovot (IL); Shmuel Bukshpan, Rehovot (IL); Michael Kardash, Rehovot (IL); Lior Cohen, Rehovot (IL)

(73) Assignee: GE Medical Systems Israel LTD, (IL)

( * ) Notice: Subject to any disclaimer, the term of this patent is extended or adjusted under 35 U.S.C. 154(b) by 0 days.

(21) Appl. No.: 10/500,987

(22) PCT Filed: Jan. 5, 2003

(86) PCT No.: PCT/IL03/00016

§ 371 (c)(1),
(2), (4) Date: Mar. 7, 2005

(87) PCT Pub. No.: WO03/057001

PCT Pub. Date: Jul. 17, 2003

(65) Prior Publication Data

US 2005/0154302 A1 Jul. 14, 2005

Related U.S. Application Data

(60) Provisional application No. 60/361,091, filed on Mar. 1, 2002, provisional application No. 60/344,803, filed on Jan. 7, 2002.

(51) Int. Cl.[7] ............................................. A61B 08/00
(52) U.S. Cl. ..................................................... 600/443
(58) Field of Search ................................ 600/437–472; 73/625, 626; 367/7, 11, 130, 138

(56) References Cited

U.S. PATENT DOCUMENTS 5,293,870 A * 3/1994 Ophir et al. ................. 600/437
5,749,364 A * 5/1998 Sliwa et al. ................. 600/438

* cited by examiner

Primary Examiner—Ali Imam
(74) Attorney, Agent, or Firm—Peter Vogel, Esq.; Armstrong Teasdale LLP

(57) ABSTRACT

A system and method of mapping irregularities of hard tissue. The method includes repeatedly transmitting ultrasonic energy towards the hard tissue at a first angle of incidence, registering the origin of transmission if an echo-reflection the hard tissue is received, defining the origin of transmission in six degrees of freedom, calculating position co-ordinates for a point causing the echo-reflection and changing the origin of transmission. The method further includes compiling position co-ordinates to generate a map of the irregularities in the surface of the hard tissue. The system includes at least one ultrasonic transducer, a central processing unit and a position locator and adjustment mechanism operably connectable and configured to accomplish the disclosed method.

15 Claims, 5 Drawing Sheets

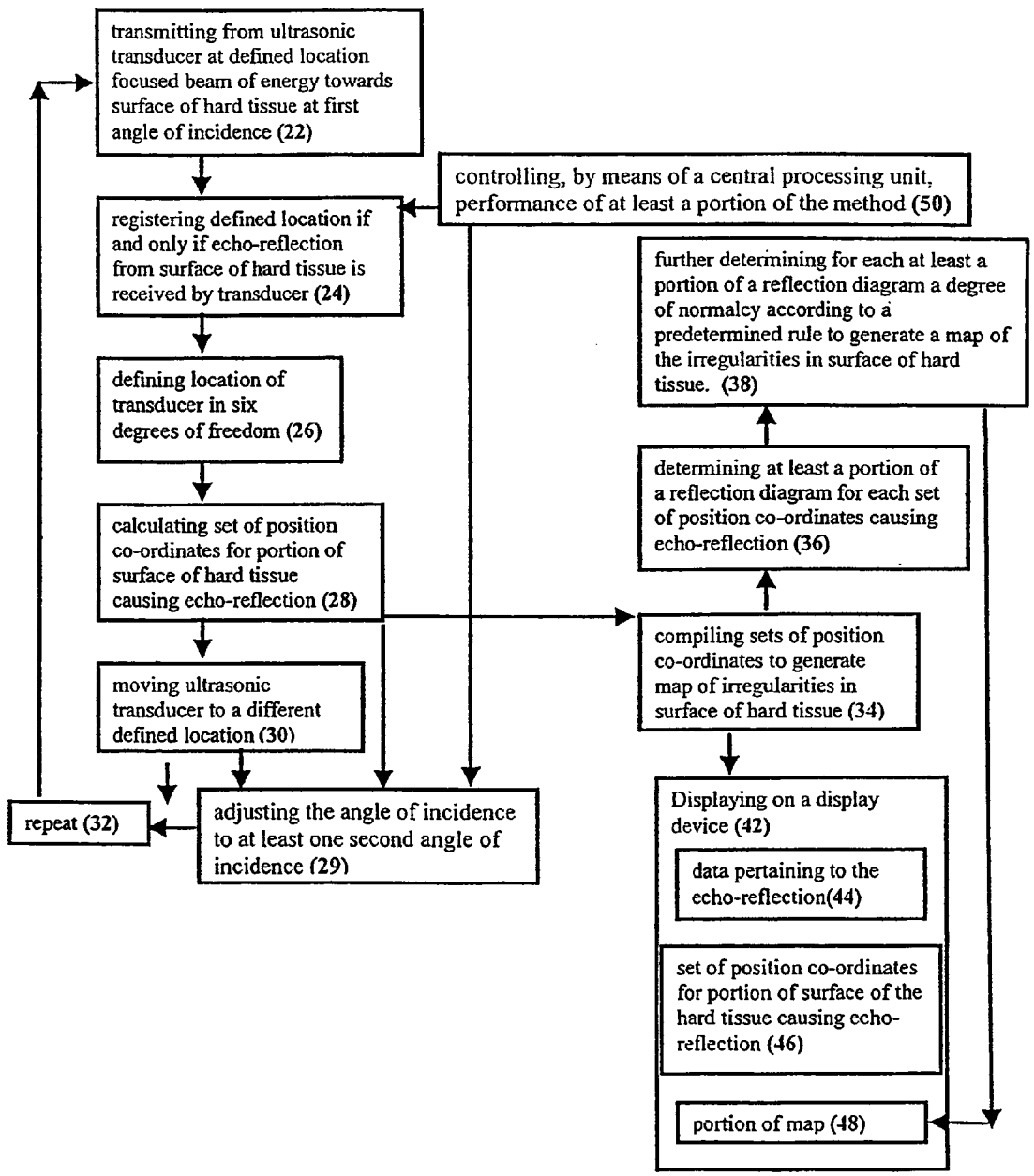

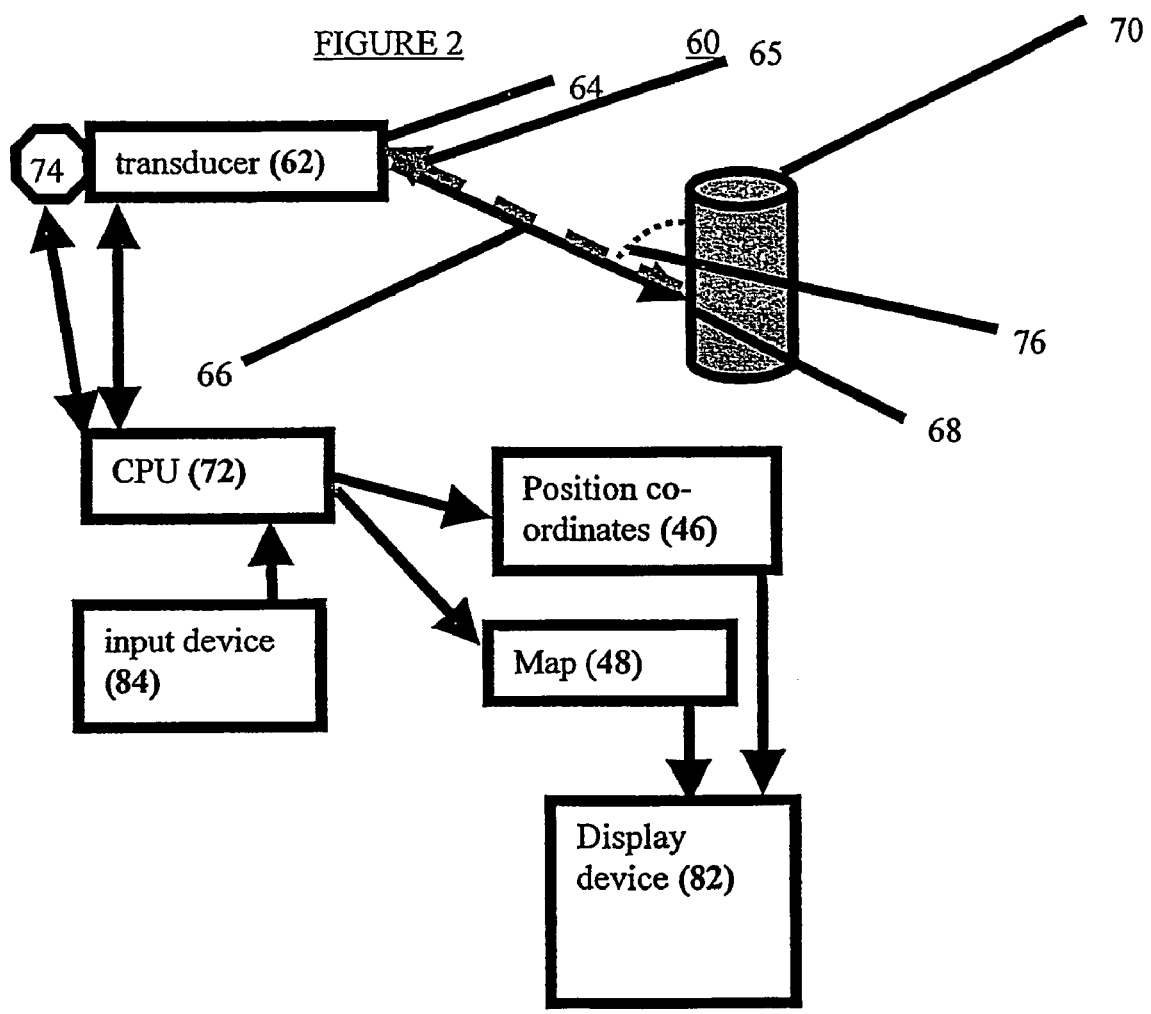

SYSTEM AND METHOD OF MAPPING IRREGULARITIES OF HARD TISSUE

This application is the U.S. National Phase under 35 U.S.C. § 371 of International Application PCT/IL03/00016, filed Jan. 5, 2003 which claims priority from U.S. Patent application 60/344,803 filed on Jan. 7, 2002 and from U.S. Patent application 60/361,091 filed on Mar. 1, 2002

FIELD AND BACKGROUND OF THE INVENTION

The present invention relates to a system and method of mapping irregularities of hard tissue. Specifically, the invention relates to detecting irregularities in hard tissue such as bone (e.g. fractures, joint abnormalities and implanted surgical anchors.)

According to the American Academy of Orthopaedic Surgeons, every year approximately 6.5 million bone fracture cases are diagnosed in the United States alone. Orthopedic medicine has traditionally relied upon radiographic images (e.g. X-Ray or CT scan) of bone tissue as a means of diagnosing bone abnormalities including fractures and malformations. These methods require exposing a patient to radiation.

U.S. Pat. No. 4,798,210 issued to Ledley describes a method for developing a 3D image of a 3D object using ultrasound whereby a first image is combined with a second image in order to create a 3D image. Again, teachings of Ledley contain neither a hint nor suggestion that renderings of bone or imperfections therein may be produced by ultrasound.

U.S. Pat. No. 5,924,989 issued to Polz is an additional example of a three dimensional ultrasonic system for capturing images of dynamic organs such as the heart or other parts of the respiratory system. Like Ledley, Polz employs a combination of different images in order to complete the three dimensional image. Again, teachings of Polz contain neither a hint nor suggestion that renderings of bone or imperfections therein may be produced by ultrasound.

U.S. Pat. No. 5,928,151 issued to Hossack et al. is a further example of a three dimensional ultrasonic scanning system. Again, teachings of this patent contain neither a hint nor suggestion that renderings of bone or imperfections therein may be produced by ultrasound. The opposite is true, the emphasis on the ability to work without contrast agents suggests that Hossack envisioned only soft tissue applications.

U.S. Pat. No. 6,120,453 issued to Sharp is a three-dimensional ultrasound system. The teachings of this patent are similar to those of Ledley and Polz. Again, Sharp employs the combination of several images to create a three dimensional image. Again, Sharp offers neither a hint nor suggestion that renderings of bone or imperfections therein may be produced by ultrasound.

In summary, none of the patents in this first group even imply that generation maps of irregularities of bone can be generated using ultrasound technology. Instead, they stress various means of increasing resolution of 3D images of soft tissue. Application of these methods directly to hard tissue is impractical because the echo reflection properties of soft tissue are not similar to those of hard tissue.

The concept of ultrasonic imaging of bone is also not unknown. However, bone images produced by ultrasound are typically not three dimensional as exemplified by this second group of prior art references.

U.S. Pat. No. 4,476,873 issued to Sorenson et al. is an ultrasound scanning system used for imaging skeletal structure. This scanning system can distinguish between hard and soft tissue and is used to detect scoliosis. However, FIGS. 14–18 of this patent make it abundantly clear that while data may be collected in three dimensions, output is supplied as graphs. Thus, it is an inherent disadvantage of Sorenson that images are not provided as a result of the scan. Sorenson teaches differentiation between lungs containing air and bones. It will be appreciated that lung tissue, which presents alternating layers of air and soft tissue, is more different from bone than other soft tissues such as muscle. Further, Sorenson teaches that Snell's law typically causes most transmitted energy to be reflected along a line which is at an angle to a longitudinal axis of the transmitting transducer. Therefore, Sorenson teaches extensive amplification of the small amount of reflected energy returning along this axis or, in the alternative, capture of reflected energy at one or more additional transducers. Thus, Sorenson teaches determination of co-ordinates of a point in three degrees of freedom, as opposed to six degrees of freedom. Thus changes in an angle of a surface over distance are not determined by these teachings. This is a distinct and inherent disadvantage which renders these teachings unsuitable to use in imaging surface irregularities of long bones.

U.S. Pat. No. 5,140,988 issued to Stouffer et al. is a method and apparatus for imaging bone structures in animal carcasses. FIGS. 2 and 3 of this patent demonstrate that the teachings of Stouffer relate to 2 dimensional images of bone. Stouffer fails to teach imaging of irregularities in bone surface such as fractures.

U.S. Pat. No. 5,840,029 issued to Mazess et al is a method for using ultrasound to measure bone. Mazess concerns himself primarily with measurement of bone properties. Mazess fails to teach imaging of irregularities in bone surface such as fractures.

U.S. Pat. No. 5,879,301 issued to Chibrera et al. is a method for detecting the properties of bone using ultrasound, specifically for detecting osteoporosis. It is an inherent disadvantage of Chibrera that production of images of measured bones, or surface irregularities thereof is not taught.

U.S. Pat. No. 6,015,383 issued to Buhler et al. teaches acoustic analysis to detect the characteristics of bone tissue where the edge of the bone is detected. However, FIGS. 3–6 of this patent make it abundantly clear that output is supplied as graphs. Thus, it is an inherent disadvantage of Buhler that images are not provided as a result of the scan.

U.S. Pat. No. 322,507 issued to Passi et al. is an ultrasonic system for evaluation of bone tissue. Like other patents in this group, it has the inherent disadvantage of providing output as graphs rather than images. Further, measurements according to these teachings are of acoustic properties and not of surface position co-ordinates.

Thus, while members of this second group of patents teach assays of bone using ultrasound technology, they fail to teach production of maps of surface irregularities in bone.

Additional patents dealing with ultrasonic imaging of bone are presented hereinbelow.

U.S. Pat. No. 5,305,752 issued to Spivey is a system for imaging tissue in the body using acoustic waves. While Spivey teaches formation of a single ultrasonic image depicting both soft tissue and bone, the image is a cross-sectional image (i.e. 2 dimensional). Spivey does not teach imaging of surface irregularities such as fractures.

U.S. Pat. No. 5,465,722 issued to Fort et al. relates to a 3D ultrasonic system. Although these teachings included production of a 3D image of a bone (FIG. 13), they do not include imaging of surface irregularities such as fractures. U.S. Pat. No. 6,375,616 issued to Soferman et al. is a method for determining fetal weight in utero. Although Soferman teaches application of grey level threshold in order to isolate bones from other tissue in an image, his teachings do not include imaging of surface irregularities such as fractures.

U.S. Pat. No. 6,390,982 issued to Bova et al. is a method of creating a three dimensional image. The teachings of Bova are directed to ultrasonic probes as an adjunct to a second imaging technology in localizing bone. This means that generation of the three dimensional image from ultrasound image data alone is beyond the scope of Bova's teachings. Further, Bova does not teach imaging of surface irregularities such as fractures.

U.S. Pat. No. 6,413,215 issued to Wu et al. is an ultrasonic system for detecting the wear of artificial joints. The teachings of Wu rely upon scattering of ultrasonic energy as a result of cavitation events in synovial fluid. Further, Wu teaches output of data as particle size information, not particle position. In summary, these teachings have little relevance to the instant application because cavitation events are not expected to occur in typical measurement of hard tissue surface irregularities.

There is thus a widely recognized need for, and it would be highly advantageous to have, a system and method mapping irregularities of hard tissue devoid of the above limitations.

SUMMARY OF THE INVENTION

According to one aspect of the present invention there is provided a method of mapping irregularities in a surface of a hard tissue within a target. The method includes: (a) transmitting from an ultrasonic transducer at a defined location a focused beam of ultrasonic energy towards the surface of the hard tissue at a first oblique angle of incidence; (b) registering the defined location if and only if an echo-reflection from the surface of the hard tissue is received by the transducer; (c) defining the location of the transducer in six degrees of freedom; (d) calculating a set of position co-ordinates for a portion of the surface of the hard tissue causing the echo-reflection; (e) moving the ultrasonic transducer to a different defined location; (f) repeating a through e; (g) repeating steps (a) through (f) with an additional angle at least 20 degrees apart from the previous oblique angle; (h) determining for each of said set of position co-ordinates for a portion of the surface of the hard tissue causing said echo-reflection at least a portion of a reflection diagram (i) further determining for each of said at least a portion of a reflection diagram a degree of normalcy according to a predetermined rule to generate a map of the irregularities in the surface of the tissue; (j) classifying any of said set of position co-ordinates for a portion of the surface of the hard tissue wherein said at least a portion of a reflection diagram is characterized by a low degree of normalcy according to said predetermined rule as belonging to a surface irregularity; and (k) compiling at least a portion of the sets of position co-ordinates to generate a map of the irregularities in the surface of the hard tissue.

According to another aspect of the present invention there is provided a system for mapping irregularities in a surface of a hard tissue within a target. The system includes at least one ultrasonic transducer, a position locator and adjustment mechanism and a central processing unit. The at least one transducer is positioned at a defined location and is capable of transmitting a focused beam of ultrasonic energy towards the surface of the hard tissue at a first oblique angle of incidence and is further capable of receiving at least a portion of the energy as an echo-reflection from the surface of the hard tissue and is further capable of communication with the central processing unit. The position locator and adjustment mechanism is operably connectable to the at least one transducer and is designed and constructed to be capable of adjusting the oblique angle of incidence between the focused beam and the surface of the hard tissue in response to a command from the central processing unit; and to be further capable of defining the location of the transducer as a set of position co-ordinates in six degrees of freedom and transmitting the set of co-ordinates to a central processing unit and to be further capable of moving the at least one ultrasonic transducer to a series of different defined location. The central processing unit designed and configured to be capable of receiving the set of position co-ordinates defining the location of the at least one transducer from the position locator and adjustment mechanism and to be further capable of calculating an additional set of position co-ordinates for a portion of the surface of the hard tissue causing the echo-reflection and to be further capable of compiling a plurality of the sets of position co-ordinates to generate a map of the surface of the hard tissue.

According to further features in preferred embodiments of the invention described below, the method further includes: (h) determining for each of the set of position co-ordinates for a portion of the surface of the hard tissue causing the echo-reflection at least a portion of a reflection diagram; (i) further determining for each of the at least a portion of a reflection diagram a degree of normalcy according to a predetermined rule to generate a map of the irregularities in the surface of the tissue; and (j) classifying any of the set of position co-ordinates for a portion of the surface of the hard tissue wherein the at least a portion of a reflection diagram is characterized by a low degree of normalcy according to the predetermined rule as belonging to a surface irregularity.

According to still further features in the described preferred embodiments repeating includes adjusting the oblique angle of incidence to at least one second oblique angle of incidence.

According to still further features in the described preferred embodiments the method further includes controlling, by means of a central processing unit, performance of at least a portion of the method.

According to still further features in the described preferred embodiments controlling includes at least one item selected from the group consisting of the adjusting and the registering.

According to still further features in the described preferred embodiments controlling indicates at least one control mechanism selected from the group consisting of mechanical control, selection from an array and electronic control.

According to still further features in the described preferred embodiments at least one item selected from the group consisting of the adjusting and the registering is performed manually by a practitioner of the method.

According to still further features in the described preferred embodiments the central processing unit is further designed and constructed to be capable of transmitting a command to the position locator and adjustment mechanism to cause the at least one transducer to move to the series of different defined locations.

According to still further features in the described preferred embodiments the command is selected from the group consisting of a command to a mechanical control, a command to switch to a different transducer of the at least one transducer and a command to an electronic control.

According to still further features in the described preferred embodiments the position locator and adjustment mechanism is designed and configured to receive input from an operator of the system, the input being selected from the group consisting of a manual position adjustment by an operator of the system and at least one instruction transmitted to the central processing unit by the operator.

According to still further features in the described preferred embodiments method further includes displaying upon a display device at least one item selected from the group consisting of: (i) data pertaining to the echo-reflection; (ii) the set of position co-ordinates for the portion of the surface of the hard tissue causing the echo-reflection; and (iii) at least a portion of the map.

According to still further features in the described preferred embodiments the map is a two dimensional map.

The present invention successfully addresses the shortcomings of the presently known configurations by providing a system and method of mapping irregularities of hard tissue such as imperfections in bone (e.g. fractures, joint abnormalities and implanted surgical anchors.)

Implementation of the method and system of the present invention involves performing or completing selected tasks or steps manually, automatically, or a combination thereof. Moreover, according to actual instrumentation and equipment of preferred embodiments of the method and system of the present invention, several selected steps could be implemented by hardware or by software on any operating system of any firmware or a combination thereof. For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a simplified flow diagram showing a sequence of events performed in execution of a method according to the present invention.

FIG. 2 is a schematic representation of a system according to the present invention.

DESCRIPTION OF THE PREFERRED EMBODIMENTS

Figure 3A:
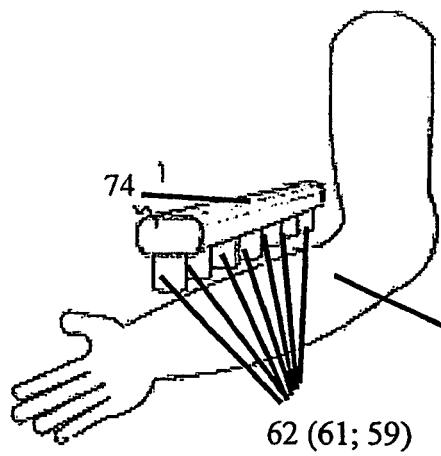
FIGS. 3a–c illustrate arrangement of ultrasonic transducers in arrays for use in the context of the present invention.

The present invention is of a system and method of mapping irregularities of hard tissue that can be used to detect imperfections in bone.

Specifically, the present invention can be used to provide maps of fractures, joint abnormalities and implanted surgical anchors.

The principles and operation of a system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 3B:
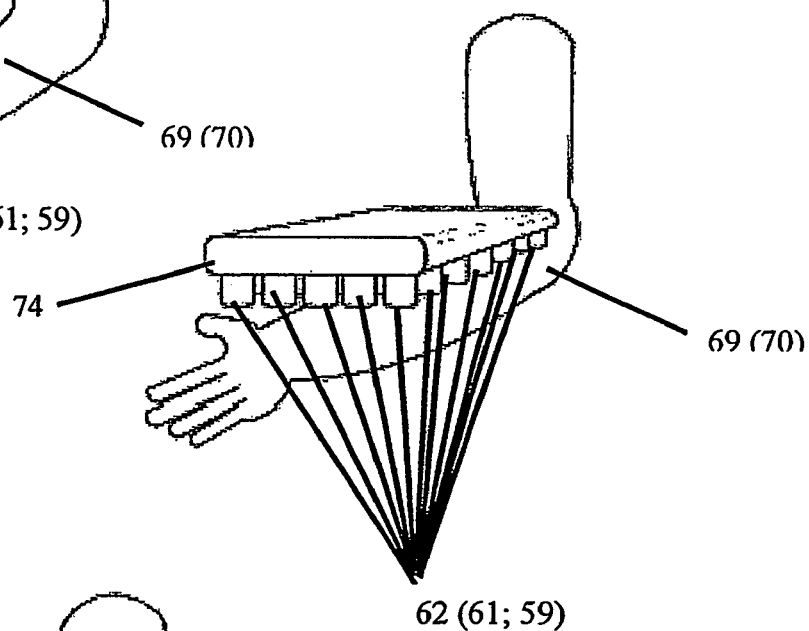
Figure 3C:
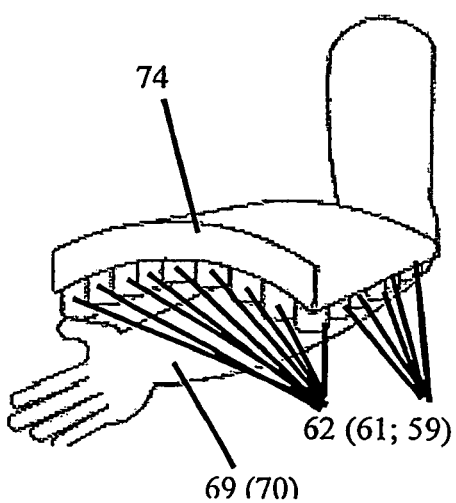

The present invention is preferentially embodied by a method 20 (FIG. 1) of mapping irregularities in a surface 68 (FIG. 2) of a hard tissue 70 within a target 69 (FIG. 3). Target 69 may include, for example, skin, fat, muscles, blood vessels, internal organs, and any other substantially soft, fluid, or low density biological tissue. Method 20 includes transmitting 22 from an ultrasonic transducer 62 at a defined location 64 a focused beam 66 of ultrasonic energy towards surface 68 of hard tissue 70 at a first oblique angle 76 of incidence.

For purposes of this specification and the accompanying claims, the term "ultrasonic" pertains to sound waves with a frequency in excess of approximately 20 kHz, more preferably in the range of 1 MHz to 20 MHz.

For purposes of this specification and the accompanying claims, the term "focused" means that a majority of transmitted energy is concentrated within a defined area surrounding an axis of a transmitted beam. Focusing may be caused by interference of a plurality of transmitted beams. Depending upon the arrangement of the transmitting transducers, this interference may involve a temporal component (i.e. transducers located further from the target transmitting earlier, those located closer to the target transmitting later) as well as a spatial component.

For purposes of this specification and the accompanying claims, the term "beam" indicates a ray of energy transmitted from one or more sources.

According to preferred embodiments of the invention, beam 66 is preferably a pulsed beam. For purposes of this specification and the accompanying claims, the term "pulsed" means temporally defined.

For purposes of this specification and the accompanying claims, the term "hard tissue" includes, but is not limited to bone such as cortical bone or trebicular bone. Bone refers to calcified fully developed bone capable of generating an ultrasonic echo-reflection in approximate accordance with Snell's law. While a developing fetus may have bones, these fetal bones are excluded from the definition of hard tissue because they are primarily cartilaginous, significant calcification typically taking place well after parturition.

Method 20 further includes registering 24 defined location 64 if and only if an echo-reflection 65 from surface 68 of hard tissue 70 is received by transducer 62.

Method 20 further includes defining 26 location 64 of transducer 62 in six degrees of freedom.

Method 20 further includes calculating 28 a set of position co-ordinates 46 for a portion of surface 68 of hard tissue 70 causing echo-reflection 65.

Method 20 further includes moving 30 ultrasonic transducer 62 to a different defined location 64.

Method 20 further includes repeating 32 the sequence of transmitting 22, registering 24, defining 26 and calculating 28. Repeating 32 may include, but is not limited to, adjusting 29 oblique angle of incidence 76 to at least one second oblique angle of incidence 76. Additional angle 76 is preferably at least 20 degrees apart from first angle 76.

Method 20 further includes compiling at least a portion of the sets of position co-ordinates 46 to generate a map 48 of the irregularities in surface 68 of hard tissue 70.

Preferably, method 20 further includes determining 36 for each set of position co-ordinates 46 for a portion of surface 68 of hard tissue 70 causing echo-reflection 65 at least a portion of a reflection diagram. For purposes of this specification and the accompanying claims, the phrase "reflection diagram" of a point on surface 68 of hard tissue 70 refers to a diagram illustrating the ratio between reflected energy 65 and transmitted energy 66 of an ultrasound beam transmitted towards that point on surface 68 of hard tissue 70 as a function of the different angles of incidence 76 between beam 66 and surface 68. Examples of ways in which reflection diagrams of this type may be useful in mapping irregularities in surface 68 are presented in FIGS. 4a–d and 5a–d.

Method 20 and system 60 rely upon the fact that surface 68 of hard tissue 70 may be considered a specular reflector (FIG. 4a) provided that it does not include any corrugations (86; FIGS. 4c, 4d, 5b and 5d) on a scale comparable with the wavelength of ultrasonic beam 66 or lower. If surface 68 of hard tissue 70 exhibits one or more irregularities 86, such as pathological discontinuities or inhomogeneities such as a fracture, rupture, crack, or tear (FIGS. 4c and 5c). Irregularity 86 may cause ultrasound beam 66 to be redirected or scattered to various directions (65; FIGS. 4c and 4d and dark shaded areas; FIGS. 5a–5d) possibly including toward ultrasound source 62, in addition to, or instead of, specular reflection.

Hard tissue 70 includes any biological material which is, under normal conditions, substantially in a solid state. In humans, hard tissue 70 includes, for example, bones, cartilage, tendons, teeth, and nails. In nonhuman organisms hard tissue 70 further includes, but is not limited to, tusks, horns, claws and shells.

Irregularities 86 in surface 68 of hard tissue 70 may be caused by a wide variety of pathologies. These pathologies include, but are not limited to, pathological discontinuities and inhomogeneities, for example, fractures, ruptures, cracks and tears. Human bone fractures, for instance, frequently occur due to a trauma event (e.g. fall, blow or other impact), due to ongoing stress exerted on the bone (e.g. athletic or military activity), or due to bone deterioration. Bone deterioration (e.g. osteoporosis), is often a result of aging.

FIGS. 4a–4d illustrate various examples of the path of an ultrasound beam 66 transmitted through a soft tissue target 69 toward a hard tissue 70 under examination. For illustration purposes, beam 66 is portrayed as a line (arrow indicates direction of wave propagation), although it is understood that in reality beam 66 has a certain width or volume which may furthermore change as beam 66 progresses.

Figure 4A:
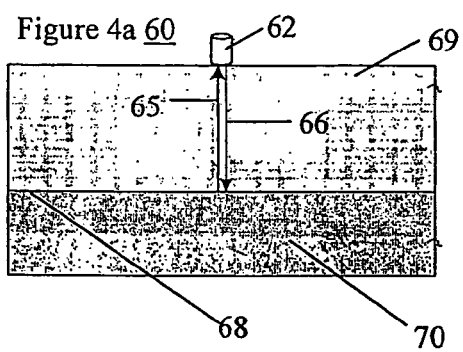
FIGS. 4a–4d illustrate echo reflection of an ultrasound beam transmitted through soft tissue toward a hard tissue according to the present invention.

Referring now to FIG. 4a, it is well known that if ultrasound beam 66 is transmitted perpendicularly, i.e. in a normal incidence, to surface 68 of hard tissue 70 whose dimensions are greater than a width of beam 66, then the ultrasonic energy will be partially reflected 65 toward ultrasound source 62.

Figure 4B:
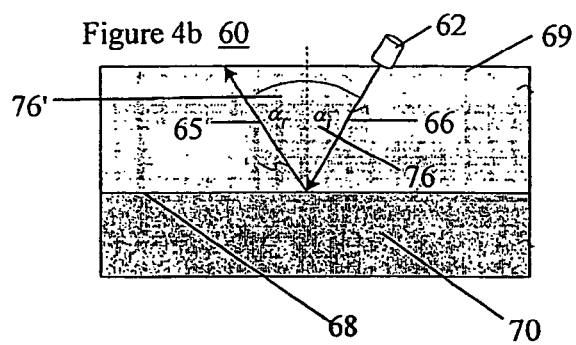
Figure 4C:
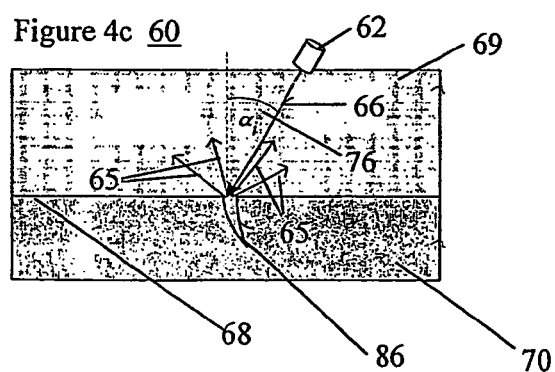
Figure 4D:
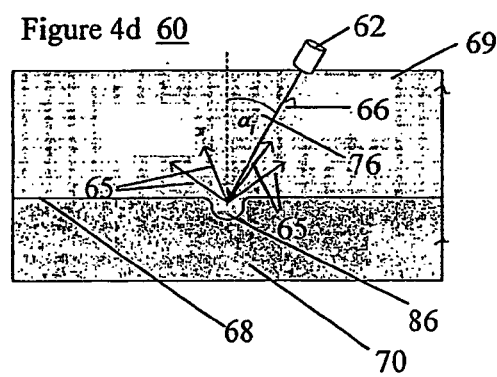

Referring now to FIG. 4b, it is also well known that, in general, as the angle of incidence 76 $\alpha_i$ (relative to the normal incidence) is increased, the amount of energy reflected 65 toward ultrasound source 62 decreases. If the angle of incidence 76 $\alpha_i$ is substantially different than 0° (the normal incidence), then energy will be reflected 65 away from source 62 in an angle of reflection 76' $\alpha_r$ which is substantially equal to angle of incidence 76 $\alpha_i$. The reflection mentioned in connection to FIGS. 4a and 4b is often referred to as "specular reflection". A surface 68 of hard tissue 70 may be considered a specular reflector provided that it does not include any corrugations on a scale comparable with the wavelength of ultrasonic beam 66 or lower.

Referring now to FIGS. 4c and 4d, if the hard tissue 70 exhibits one or more surface irregularities 86 (e.g. pathological discontinuity, inhomogeneity, fracture, rupture, crack, or tear), irregularity 86 may cause reflection 65 of beam 66 to be redirected or scattered to various directions possibly including toward ultrasound source 62. This scattering is referred to as "nonspecular reflection".

In reducing the present invention to practice, it has been determined that the degree to which reflection 65 is scattered (i.e. nonspecular) is indicative of the nature of irregularity 86. Conversely, the degree to which reflection 65 is specular is indicative of the smoothness of surface 68.

Referring now to FIG. 4d, it should be noted that surface 68 of even a healthy hard tissue 70 is not perfectly flat, but rather exhibits local convexities, concavities, curves, and other types of geometries in various sizes and shapes which are attributable to the natural anatomy of hard tissue 70. Such anatomical geometries, though not related to any pathology, may also cause reflection 65 of beam 66 to be redirected or scattered to various directions possibly including toward ultrasound source 62.

Reflections 65 of ultrasonic energy 66 from a pathological discontinuity or inhomogeneity 86 (FIG. 4c), whether specular or nonspecular will be referred to hereinunder as "pathology echoes", and ultrasonic energy reflected, specularly or nonspecularly, from an anatomical geometry 86 (FIG. 4d), will be referred to hereinunder as "geometrical echoes".

Since echo reflections 65 from a healthy and substantially flat surface 68 of hard tissue 70 are primarily specular (i.e. their reflection is primarily limited to a certain angle of reflection) whereas pathology echoes and geometrical echoes are often both specular and nonspecular, it follows that reflection diagrams (as defined hereinabove) of a pathological discontinuity (86; FIGS. 4c and 5c) and an anatomical geometry (86; FIGS. 4d and 5d) are each differentiable from a reflection diagram of a healthy and substantially flat hard tissue 70.

The extent of nonspecular reflection caused by a certain reflector on surface 68 of hard tissue 70, such as a pathological discontinuity or an anatomical geometry, depends on several factors. Those factors include, but are not limited to the size, shape and smoothness or roughness of the reflector, the wavelength of incident beam 66, and angle of incidence 76. Pathological discontinuities and inhomogeneities such as fractures have a typically different size, shape and roughness than anatomical geometries. Thus, in reducing the present invention to practice, it has been determined that reflection diagrams of pathological discontinuities and inhomogeneities are differentiable from those of anatomical geometries.

FIG. 5a to 5d illustrate examples of reflection diagrams of various reflectors on surface 68 of hard tissue 70. In the drawings, each dark area represents a range of incidence angles where specular or nonspecular reflection toward the ultrasound source approaches a maximum. It is understood that although, for illustration purposes, the diagrams are portrayed in two dimensions only, in reality reflection occurs in three dimensions; thus, for example, what appears in the drawings as a segment of a circle may resemble in reality a segment of a hemisphere.

Figure 5A:
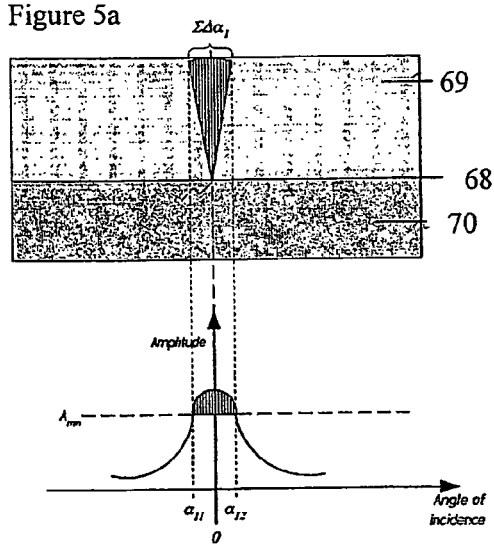
FIGS. 5a–5d illustrate reflection diagrams resulting from reflections presented in FIG. 4.

Referring now to FIG. 5a, there is illustrated an example of a reflection diagram of a healthy and substantially flat area on surface 68 of hard tissue 70. In such a case, the maximal amplitude of returning echo 65 (FIG. 4a) is around the normal incidence that is, in the current example, between angles of incidence $\alpha_{11}$ and $\alpha_{12}$. Therefore, it is evident that reflection from a substantially flat reflector is strongly angle-dependent.

Figure 5B:
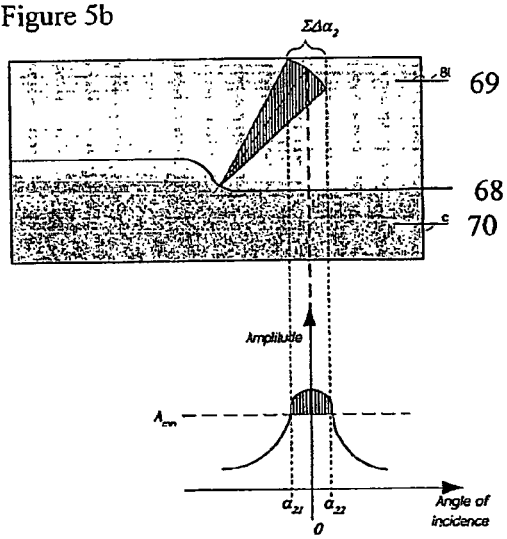
Figure 5C:
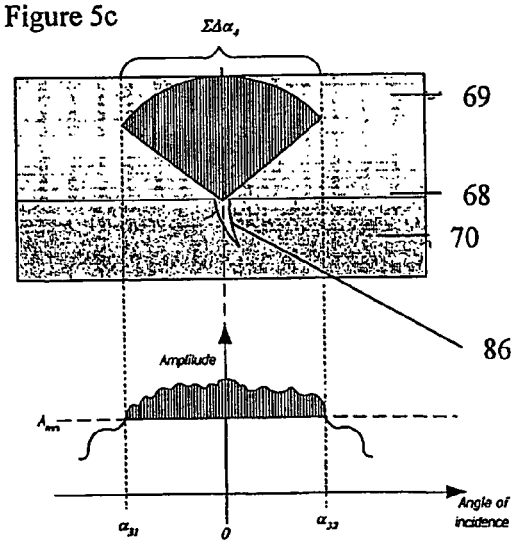
Figure 5D:
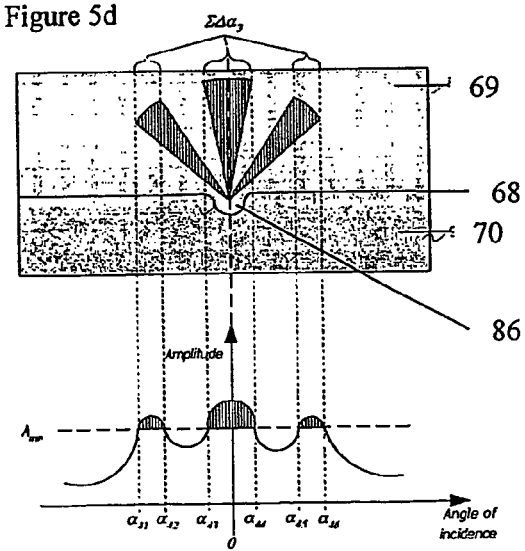

Referring to FIG. 5b, there is illustrated an example of a reflection diagram of a slightly curved area on surface 68 of hard tissue 70. As long as the gradient about the area of incidence is low relative to the wavelength of incident beam 66 and provided that the local surface is sufficiently smooth, the maximal amplitude of the returning echo remains around the locally defined normal incidence that is, in the current example, between $\alpha_{21}$ and $\alpha_{22}$. Thus, it can be seen that reflection from a curved surface that is characterized with a low gradient relative to the wavelength of the ultrasound beam, is strongly angle-dependent like the reflection diagram produced by a flat surface.

Referring to FIG. 5c, there is illustrated an example of a reflection diagram of a pathological discontinuity 86 on surface 68 of hard tissue 70. Discontinuity 86 may include, for example, a fracture, rupture, crack, tear or other pathology recited hereinabove. The present invention relies on the principle that the reflection diagram of pathological discontinuity 86 remains approximately maximum throughout a relatively wide range of angles of incidence such as, in the current example, from $\alpha_{31}$ through $\alpha_{32}$. Moreover, scattering caused by pathological discontinuity 86 tends towards uniformity throughout a relatively wide range of angles of incidence ($\alpha$). Thus, pathological discontinuity is characterized by a reflection diagram which is largely angle independent.

Referring to FIG. 5d, there is illustrated an example of a reflection diagram of an anatomical geometry 86 on surface 68 of hard tissue 70, for example, a local concavity. The reflection diagram of anatomical geometries in healthy hard tissue 70 typically exhibit one or more distinct local extrema such as, in the current example, a first local maximum between $\alpha_{41}$ and $\alpha_{42}$, a second local maximum between $\alpha_{43}$ and $\alpha_{44}$, and a third local maximum between $\alpha_{45}$ and $\alpha_{46}$. Thus, nonspecular reflection from a healthy hard tissue 70 surface which includes an anatomical geometry 86 is angle-dependent like the flat or slightly curved surfaces of FIGS. 5a and 5b, although to a lesser degree.

In summary, the reflection diagram of a pathological discontinuity or inhomogeneity 86 on surface 68 of hard tissue 70 is typically wider and more uniform, i.e. less angle-dependent, than the reflection diagram of a healthy hard tissue 70. This is true even if the reflection diagram is compared to one resulting from an anatomical geometry. More specifically, a pathological discontinuity or inhomogeneity causes nonspecular reflection toward the ultrasound source over a wider range of angles of incidence than does healthy tissue with or without an anatomical geometry. Further, nonspecular reflection from a pathological discontinuity or inhomogeneity remains near maximum (i.e. is largely angle independent) throughout a relatively wide range of angles of incidence, whereas reflection from an anatomical geometry typically exhibits one or more local extrema (i.e. is largely angle dependent).

It is therefore a particular and fundamental feature of the present invention that it enables detection, and consequently location, mapping and imaging of pathological discontinuities and inhomogeneities on a surface 68 of hard tissue 70 based upon analysis of reflection diagrams thereof and comparison to reflection diagrams produced by adjacent surface 68 of healthy hard tissue 70.

Preferably, method 20 includes further determining 38 for each of the at least a portion of a reflection diagram a degree of normalcy according to a predetermined rule to generate a map of the irregularities in surface 68 of hard tissue 70. Thus, method 20 optionally but preferably includes classifying any of position co-ordinates 46 for surface 68 of hard tissue 70 wherein the at least a portion of a reflection diagram is characterized by a low degree of normalcy according to the predetermined rule as belonging to a surface irregularity.

Preferably, method 20 further includes controlling 50, by means of a central processing unit 72, performance of at least a portion of method 20. Controlling 50 include, for example, adjusting 29 or registering 24. Controlling 50 may be accomplished, for example, employing a mechanical control mechanism, selection from an array or electronic control. Examples of arrays of transducers 62 suited for use in the present invention are presented in FIGS. 3a–c. Use of arrays to accomplish moving 30 greatly increases the speed with which position co-ordinates 46 and map 48 may be generated.

Optionally, but also preferably, portions of method 20 (e.g. adjusting 29 and/or registering 24) may be performed manually by a practitioner thereof The present invention is thus further embodied by system 60 for mapping irregularities in surface 68 of hard tissue 70 within a target. System 60 includes at least one transducer 62, a position locator and adjustment mechanism 74 and central processing unit 72.

Transducer 62 is positioned at defined location 64 and is capable of transmitting focused beam 66 of ultrasonic energy towards surface 68 of hard tissue 70 at first angle 76 of incidence. Transducer 62 is further capable of receiving at least a portion 65 of the energy as an echo-reflection from the surface 68 of hard tissue 70. Transducer 62 is further capable of communication with central processing unit 72 for purposes of transmission and receipt of data. This data may include positional information (e.g. 64 or 76 or 46) as well as commands.

Position locator and adjustment mechanism 74 is operably connectable to, or integrally formed with, transducer(s) 62 and is designed and constructed to be capable of adjusting 29 oblique angle of incidence 76 between focused beam 66 and surface 68 of hard tissue 70 in response to a command from central processing unit 72.

Position locator and adjustment mechanism 74 is further capable of defining 26 the location of the transducer 62 as a set of position co-ordinates 64 in six degrees of freedom and transmitting the set of co-ordinates 64 to central processing unit 72. Position locator and adjustment mechanism 74 is further capable of moving 30 transducer 62 to a series of different defined locations 64.

Central processing unit 72 is designed and configured to be capable of receiving position co-ordinates 64 defining the location of transducer 62 from position locator and adjustment mechanism 74 and to be further capable of calculating 28 an additional set of position co-ordinates 46 for a portion of surface 68 of hard tissue 70 causing echo-reflection 65 and to be further capable of compiling 34 a plurality of the sets of position co-ordinates to generate a map of the surface of the hard tissue.

Central processing unit 72 may be, for example, a computer such as a personal computer (PC) having an operating system such as DOS, Windows™, OS/2™ or Linux; Macintosh™, Palm OS™, an EPOC™ computer; a computer having JAVA™-OS as the operating system; a graphical workstations such as a computer of Sun Microsystems™ or Silicon Graphics™, or another computer having some version of the UNIX operating system such as AIX™ or SOLARIS™ of Sun Microsystems™; or any other known and available operating system, or a personal digital assistant (PDA), each of which is known to include an inherent or connectable display device 82.

Optionally, but also preferably, central processing unit 72 is further designed and configured to be capable of transmitting a command to position locator and adjustment mechanism 74 to cause at least one transducer 62 to move 30 to a series of different defined locations 64. The command may be, for example a command to a mechanical control, a command to switch to a different transducer 62 an array of transducers 62 (see FIGS. 3a–c) or a command to an electronic control.

Alternately, but also preferably, position locator and adjustment mechanism 74 is designed and configured to receive input from an operator of system 60. The input may include, for example, a manual position adjustment of transducer 62 by an operator of system 60. Alternately or additionally, the input may include at least one instruction transmitted to central processing unit 72 by the operator. Instructions may be transmitted by means of input device 84 which is preferably a part of system 60. Input device 84 may be any device for entry of data to a computing device such as CPU 72. Therefore, input device 82 may include, but is not limited to, a keyboard, a computer mouse, a trackpad, a track ball, a stylus, a touchscreen or a microphone.

Thus, method 20 preferably further includes displaying data upon a display device 82 preferably included in system 60. Display device 82 may include any device which visually presents data to a user. Therefore, display device 82 may be, for example, a cathode ray tube display screen, a liquid crystal display (e.g. active matrix or passive matrix), a plasma screen, a printout or an array of light emitting diodes. The data 44 displayed upon device 82 preferably pertains to echo-reflection 65 and may include one or more set(s) of position co-ordinates 46 corresponding to a portion of the surface 68 of hard tissue 70 causing echo-reflection 65 and/or at least a portion of map 48. Map 48 is preferably two dimensional.

Thus, the present invention works most effectively when each point or area on surface 68 of hard tissue 70 is examined from a variety of angles of incidence 76 rather than from one or more specific angle of incidence 76. Further, the greater the number of angles of incidence 76 employed the greater the ability to discern irregularities in surface 68. Moreover, it is a particular feature of the present invention, that the decision whether or not a certain area on surface 68 of hard tissue 70 area exhibits a pathological discontinuity or inhomogeneity is based on an analysis of echoes of signals transmitted in a wide range of angles of incidence 76 rather than in one or more specific angles of incidence. Thus, the greater the range of angles of incidence 76, the greater the ability to discern irregularities in surface 68. As a result, the present invention eliminates the need to determine or estimate the orientation of the hard tissue 70 throughout the scanning procedure, for example, in order to maintain a specific angle of incidence with respect to the hard tissue 70. This feature is especially advantageous in cases where it is difficult to determine in vivo the orientation of the hard tissue 70 being examined, for example, due to the curved or otherwise untraceable shape of the hard tissue 70 or due to a thick layer of soft tissue interposing between the probe and the hard tissue 70.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed:

1. A method of mapping irregularities in a surface of a hard tissue within a target, the method comprising:
   (a) transmitting from an ultrasonic transducer at a defined location a focused beam of ultrasonic energy towards the surface of the hard tissue at a first oblique angle of incidence;
   (b) registering said defined location if and only if an echo-reflection from said surface of the hard tissue is received by said transducer;
   (c) defining said location of said transducer in six degrees of freedom;
   (d) calculating a set of position co-ordinates for a portion of the surface of the hard tissue causing said echo-reflection;
   (e) moving said ultrasonic transducer to a different defined location;
   (f) repeating a through e;
   (g) repeating steps (a) through (f) with an additional angle at least 20 degrees apart from the previous oblique angle;
   (h) determining for each of said set of position co-ordinates for a portion of the surface of the hard tissue causing said echo-reflection at least a portion of a reflection diagram;
   (i) further determining for each of said at least a portion of a reflection diagram a degree of normalcy according to a predetermined rule to generate a map of the irregularities in the surface of the tissue;

(j) classifying any of said set of position co-ordinates for a portion of the surface of the hard tissue wherein said at least a portion of a reflection diagram is characterized by a low degree of normalcy according to said predetermined rule as belonging to a surface irregularity; and (k) compiling at least a portion of said sets of position co-ordinates to generate a map of the irregularities in the surface of the hard tissue.

2. The method of claim 1, wherein said repeating includes adjusting said angle of incidence to at least one second angle of incidence.

3. The method of claim 2, further comprising:
(i) controlling, by means of a central processing unit, performance of at least a portion of the method.

4. The method of claim 3, wherein said controlling includes at least one item selected from the group consisting of said adjusting and said registering.

5. The method of claim 4, wherein said controlling indicates at least one control mechanism selected from the group consisting of mechanical control, selection from an array and electronic control.

6. The method of claim 1, further comprising:
(l) displaying upon a display device at least one item selected from the group consisting of:
   (i) data pertaining to said echo-reflection;
   (ii) said set of position co-ordinates for said portion of the surface of the hard tissue causing said echo-reflection; and
   (iii) at least a portion of said map.

7. The method of claim 1, further comprising:
(l) controlling, by means of a central processing unit, performance of at least a portion of the method.

8. The method of claim 1, wherein at least one item selected from the group consisting of said adjusting and said registering is performed manually by a practitioner of the method.

9. The method of claim 1, wherein said map is a two dimensional map.

10. A system for mapping irregularities in a surface of a hard tissue within a target, the system comprising:
(a) at least one ultrasonic transducer:
   (i) said at least one transducer positioned at a defined location;
   (ii) said at least one transducer capable of transmitting a focused beam of ultrasonic energy towards the surface of the hard tissue at a first angle of incidence;
   (iii) said at least one transducer capable of receiving at least a portion of said energy as an echo-reflection from the surface of the hard tissue; and
   (iv) said at least one transducer capable of communication with a central processing unit;
(b) a position locator and adjustment mechanism operably connectable to said at least one transducer and designed and constructed;
   (i) to be capable of adjusting said angle of incidence between said focused beam and the surface of the hard tissue in response to a command from said central processing unit;
   (ii) to be further capable of defining said location of said transducer as a set of position co-ordinates in six degrees of freedom and transmitting said set of co-ordinates to a central processing unit;
   (iii) to be further capable of moving said at least one ultrasonic transducer to a series of different defined location;
(c) said central processing unit designed and configured;
   (i) to be further capable of receiving said set of position co-ordinates defining said location of said at least one transducer from said position locator and adjustment mechanism;
   (ii) to be further capable of calculating an additional set of position co-ordinates for a portion of the surface of the hard tissue causing said echo-reflection;
   (iii) to be further capable of compiling a plurality of said sets of position co-ordinates to generate a map of the surface of the hard tissue.

11. The system of claim 10, further comprising a:
(d) a display device capable of communication with said central processor; said display device designed and constructed to perform at least one function selected from the group consisting of:
   (i) display data pertaining to said echo-reflection;
   (ii) display said additional set of position co-ordinates for a portion of the surface of the hard tissue causing said echo-reflection; and
   (iii) display at least a portion of said map.

12. The system of claim 10, wherein said central processing unit is further designed and constructed to be capable of transmitting a command to said position locator and adjustment mechanism to cause said at least one transducer to move to said series of different defined locations.

13. The system of claim 12, wherein said command is selected from the group consisting of a command to a mechanical control, a command to switch to a different transducer of said at least one transducer and a command to an electronic control.

14. The system of claim 10, wherein said position locator and adjustment mechanism is designed and configured to receive input from an operator of the system, said input being selected from the group consisting of a manual position adjustment by an operator of the system and at least one instruction transmitted to said central processing unit by said operator.

15. The system of claim 10, wherein said map is a two dimensional map.

* * * * *